(12) United States Patent
Choi et al.

(10) Patent No.: US 9,724,676 B2
(45) Date of Patent: Aug. 8, 2017

(54) OXIDATION CATALYST FOR PRODUCTION OF BUTADIENE AND METHOD OF PREPARING THE SAME

(71) Applicant: LG CHEM, LTD., Seoul (KR)

(72) Inventors: Dae Heung Choi, Daejeon (KR); Dong Hyun Ko, Daejeon (KR); Jun Han Kang, Daejeon (KR); Kyong Yong Cha, Daejeon (KR); Dae Chul Kim, Daejeon (KR); Hyun Seok Nam, Daejeon (KR); Myung Ji Suh, Daejeon (KR)

(73) Assignee: LG CHEM, LTD., Seoul (KR)

( * ) Notice: Subject to any disclaimer, the term of this patent is extended or adjusted under 35 U.S.C. 154(b) by 288 days.

(21) Appl. No.: 14/394,426

(22) PCT Filed: May 2, 2014

(86) PCT No.: PCT/KR2014/003975
§ 371 (c)(1),
(2) Date: Oct. 14, 2014

(87) PCT Pub. No.: WO2014/182026
PCT Pub. Date: Nov. 13, 2014

(65) Prior Publication Data
US 2015/0375212 A1     Dec. 31, 2015

(30) Foreign Application Priority Data

May 6, 2013   (KR) .................. 10-2013-0050472
Apr. 30, 2014  (KR) .................. 10-2014-0052327

(51) Int. Cl.

| | | |
|---|---|---|
| B01J 23/887 | (2006.01) | |
| C07C 5/48 | (2006.01) | |
| B01J 37/03 | (2006.01) | |
| B01J 23/00 | (2006.01) | |
| B01J 23/31 | (2006.01) | |
| B01J 23/34 | (2006.01) | |

(52) U.S. Cl.
CPC ......... *B01J 23/8876* (2013.01); *B01J 23/002* (2013.01); *B01J 23/31* (2013.01); *B01J 23/34* (2013.01); *B01J 37/031* (2013.01); *C07C 5/48* (2013.01); *B01J 2523/00* (2013.01); *C07C 2523/04* (2013.01); *C07C 2523/31* (2013.01); *C07C 2523/887* (2013.01)

(58) Field of Classification Search
CPC ...... B01J 23/8876; B01J 23/002; B01J 23/31; B01J 23/34; B01J 2523/00
USPC ................................ 502/305–307, 311–318
See application file for complete search history.

(56) References Cited

U.S. PATENT DOCUMENTS

| | | | |
|---|---|---|---|
| 3,972,920 A | 8/1976 | Ishii et al. | |
| 4,148,757 A * | 4/1979 | Brazdil .................. | B01J 23/002 502/204 |
| 4,424,141 A * | 1/1984 | Grasselli ................ | B01J 23/002 502/205 |
| 4,537,874 A * | 8/1985 | Sato ....................... | B01J 23/002 502/205 |
| 4,732,884 A * | 3/1988 | Sarumaru .............. | B01J 23/002 502/205 |
| 5,132,269 A | 7/1992 | Sasaki et al. | |
| 2005/0033093 A1* | 2/2005 | Teshigahara .......... | C07C 51/252 568/479 |
| 2013/0281748 A1 | 10/2013 | Cha et al. | |
| 2016/0184805 A1* | 6/2016 | Xiong .................. | B01J 23/8876 502/306 |
| 2016/0256855 A1* | 9/2016 | Choi ..................... | B01J 29/076 |

FOREIGN PATENT DOCUMENTS

| | | | | |
|---|---|---|---|---|
| EP | 2902106 A1 | | 8/2015 | |
| JP | 10114689 A | | 5/1998 | |
| JP | 2003-230836 | | 8/2003 | |
| JP | 2013-043125 | | 3/2013 | |
| KR | 10-2013-0003125 | | 1/2013 | |
| KR | 10-2013-0036470 | | 4/2013 | |
| KR | 10-2013-0003125 | * | 9/2013 | ............. C07C 5/333 |
| WO | 2013002459 A1 | | 1/2013 | |

* cited by examiner

*Primary Examiner* — Patricia L Hailey
(74) *Attorney, Agent, or Firm* — Dentons US LLP

(57) ABSTRACT

Disclosed is a multi-component bismuth molybdate catalyst for production of butadiene which comprises bismuth, molybdenum and at least one metal having a monovalent, divalent or trivalent cation, and further comprises cesium and potassium and thus has advantages of improving conversion ratio, yield and selectivity of butadiene and of providing stability of process operation.

3 Claims, No Drawings

OXIDATION CATALYST FOR PRODUCTION OF BUTADIENE AND METHOD OF PREPARING THE SAME

This application is a National Stage Entry of International Application No. PCT/KR2014/003975, filed May 2, 2014, and claims the benefit of Korean Application No. 10-2013-0050472, filed on May 6, 2013, and Korean Application No. 10-2014-0052327, filed Apr. 30, 2014, all of which are hereby incorporated by reference in their entirety for all purposes as if fully set forth herein.

TECHNICAL FIELD

The present invention relates to a multi-component bismuth molybdate catalyst for production of butadiene from a butene mixture and a method of preparing the same. More specifically, the present invention relates to a multi-component bismuth molybdate catalyst for production of butadiene comprising bismuth, molybdenum and at least one metal having a monovalent, divalent or trivalent cation, wherein the multi-component bismuth molybdate catalyst further comprises cesium and potassium, and a method of preparing the same.

BACKGROUND ART

Methods for producing 1,3-butadiene, the demand and value of which are gradually increasing as an intermediate of petrochemical products in the petrochemical industry, include naphtha cracking, direct dehydrogenation of normal-butene, and oxidative dehydrogenation of normal-butene.

Of these, oxidative dehydrogenation (ODH) of normal-butene to produce butadiene has advantages of reducing energy consumption because it is an exothermic reaction that may be performed at a low temperature, unlike direct dehydrogenation, and of inhibiting carbon deposition and removing the carbon deposits by addition of an oxidant during dehydrogenation. Various metal oxides are used as catalysts for oxidation/dehydrogenation of butane. In particular, a bismuth molybdenum-based catalyst which is a composite of bismuth oxide and molybdenum oxide is known to exhibit superior activity.

The bismuth molybdenum-based catalyst includes pure bismuth molybdate catalysts composed of only bismuth and molybdenum oxides and multi-component bismuth molybdate catalysts containing various other metals. Production of 1,3-butadiene through oxidative dehydrogenation of normal-butene in the presence of a pure bismuth molybdate catalyst is unsuitable for commercial processes due to limitation in increasing a yield of 1,3-butadiene. As an alternative to the pure bismuth molybdate catalyst, production of multi-component bismuth molybdate catalysts containing various other metals, in addition to bismuth and molybdate, is actively researched to improve activity of bismuth molybdate catalysts in oxidative dehydrogenation of normal-butene.

When only 1-butene having relatively high reactivity among normal-butenes is used as a reactant to obtain 1,3-butadiene at a high yield, or a C4 mixture containing normal-butane and normal-butene is used as a reactant in the production of 1,3-butadiene using a multi-component bismuth molybdate catalyst, very complicated multi-component bismuth molybdate catalysts including a combination of more types of metals are used. That is, metals are continuously added to improve catalytic activity, thus disadvantageously making catalyst components considerably complicated, making synthesis route for producing catalysts complicated and making it difficult to obtain reproduction. In addition, in the prior art, only pure normal-butene (1-butene or 2-butene) is used as a reactant, or a C4 mixture having a low normal-butane content less than 10% by weight is used as a reactant although a mixture of normal-butane and normal-butene is used as the reactant. Accordingly, when a C4 mixture having a high normal-butane content is used as the reactant, yield of 1,3-butadiene becomes lower.

In addition, C4 mixtures that may be easily obtained by an actual petrochemical process have a high content of normal-butane and require further separation of normal-butene so as to apply catalysts used in the prior art to commercial processes and thus inevitably cause great deterioration in economic efficiency.

DISCLOSURE

Technical Problem

Therefore, the present invention has been made in view of the above problems, and it is an object of the present invention to provide an oxidation catalyst for production of butadiene from a butene mixture, which exhibits improved conversion ratio, yield and selectivity of butadiene and secures stability of process operation in the production of butadiene from the butene mixture, a method of preparing the same and a method of preparing butadiene using the same.

The object described above and other objects of the present invention can be accomplished by the present invention described below.

Technical Solution

Therefore, in accordance with one aspect of the present invention, provided is a multi-component bismuth molybdate catalyst for production of butadiene, comprising bismuth, molybdenum and at least one metal having a monovalent, divalent or trivalent cation, wherein the multi-component bismuth molybdate catalyst further comprises cesium and potassium.

In accordance with another aspect of the present invention, provided is a method of preparing a multi-component bismuth molybdate catalyst for production of butadiene, the method comprising a) preparing a first solution comprising a bismuth precursor, a monovalent, divalent or trivalent cationic metal precursor, a potassium precursor and a cesium precursor, b) preparing a second solution in which a molybdenum precursor is dissolved, c) mixing the first solution with the second solution, d) reacting the resulting mixed solution, and e) drying the resulting reaction product.

The step c) may include adding the first solution to the second solution, followed by mixing.

The method may further include f) calcining the dried product.

In accordance with another aspect of the present invention, provided is a method of preparing a multi-component bismuth molybdate catalyst for production of butadiene, the method comprising i) preparing a first solution comprising a monovalent, divalent or trivalent cationic metal precursor, a potassium precursor and a cesium precursor, ii) preparing a second solution in which a bismuth precursor is dissolved, iii) preparing a third solution in which a molybdenum precursor is dissolved, iv) mixing the first solution with the second solution to prepare a first mixed solution, v) mixing the first mixed solution with the second solution to prepare a second mixed solution, vi) reacting the second mixed solution, and vii) drying the resulting reaction product.

The method may further include viii) calcining the dried product.

In accordance with another aspect of the present invention, provided is a method of preparing 1,3-butadiene comprising a) charging the multi-component bismuth molybdate catalyst as a fixed bed in a reactor, and b) continuously passing a reactant comprising a butene-containing C4 mixture, air and steam over the catalyst layer of the reactor to obtain 1,3-butadiene.

Advantageous Effects

As apparent from the foregoing, the present invention provides a multi-component bismuth molybdate catalyst for production of butadiene from a butene mixture which has the effects of improving yield and selectivity of butadiene and securing stability of process operation.

BEST MODE

Hereinafter, the present invention will be described in detail.

The multi-component bismuth molybdate catalyst for production of butadiene according to the present invention comprises bismuth, molybdenum and at least one metal having a monovalent, divalent or trivalent cation, wherein the multi-component bismuth molybdate catalyst further comprises cesium and potassium.

In a preferred embodiment, the present invention provides a multi-component bismuth molybdate catalyst having improved conversion ratio, yield and selectivity in the production of butadiene from butene as a starting material by adding predetermined amounts of Cs and K to a Mo—Bi—Fe—Co-based oxidation catalyst for production of butadiene from a butene mixture, and a method of preparing 1,3-butadiene from a C4 mixture containing butene using the catalyst.

The cesium and potassium are present in a molar weight ratio (Cs:K) of, for example, 1:0.001 to 1:10, 1:0.005 to 1:1, 1:0.01 to 1:0.8, or 1:0.03 to 1:0.5. Within this range, activity and selectivity of Cs and K can be considerably efficiently controlled.

In addition, the present invention provides a method of preparing a multi-component bismuth molybdate catalyst for production of butadiene, the method comprising a) preparing a first solution comprising a bismuth precursor, a monovalent, divalent or trivalent cationic metal precursor, a potassium precursor and a cesium precursor, b) preparing a second solution in which a molybdenum precursor is dissolved, c) mixing the first solution with the second solution, d) reacting the resulting mixed solution, and e) drying the resulting reaction product.

The step c) may include adding the first solution to the second solution, followed by mixing.

The method may further include f) calcining the dried product.

In addition, the present invention provides a method of preparing a multi-component bismuth molybdate catalyst for production of butadiene, the method comprising i) preparing a first solution comprising a monovalent, divalent or trivalent cationic metal precursor, a potassium precursor and a cesium precursor, ii) preparing a second solution in which a bismuth precursor is dissolved, iii) preparing a third solution in which a molybdenum precursor is dissolved, iv) mixing the first solution with the second solution to prepare a first mixed solution, v) mixing the first mixed solution with the second solution to prepare a second mixed solution, vi) reacting the second mixed solution, and vii) drying the resulting reaction product.

The method may further include viii) calcining the dried product.

There is no limitation as to the order of the steps i) to iii).

For example, the monovalent, divalent or trivalent cationic metal may comprise at least one selected from the group consisting of cobalt, zinc, magnesium, manganese, nickel, copper, iron, rubidium, sodium, aluminum, vanadium, zirconium and tungsten.

In another example, the monovalent, divalent or trivalent cationic metal may comprise at least one selected from the group consisting of cobalt, manganese, nickel and iron.

In a preferred embodiment, the monovalent, divalent or trivalent cationic metal comprises iron and cobalt.

A molar weight ratio of molybdenum to bismuth to iron to cobalt to cesium to potassium is for example 10:0.1~10: 0.1~10:1~20:0.05~5:0.01~3, 10:0.5~2:0.5~2:5~15:0.1~1: 0.01~0.5, or 10:0.8~1.2:0.8~2:6~10:0.1~0.9:0.01~0.5. Within this range, conversion ratio, selectivity and yield of the product are advantageously excellent.

That is, in a preferred embodiment, the oxidation catalyst is represented by the following general formula:

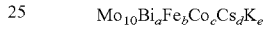

$Mo_{10}Bi_aFe_bCo_cCs_dK_e$ wherein a, b, c, d and e for example satisfy $0.1 \leq a \leq 10$, $0.1 \leq b \leq 10$, $1 \leq c \leq 20$, $0.05 \leq d \leq 5$ and $0.01 \leq e \leq 3$, respectively.

In another example, stoichiometric coefficients, i.e., a, b, c, d and e satisfy the ranges of $0.5 \leq a \leq 2$, $0.5 \leq b \leq 2$, $5 \leq c \leq 15$, $0.1 \leq d \leq 1$ and $0.05 \leq e \leq 0.5$, respectively.

There is no particular limitation as to the metal precursor for production of the multi-component bismuth molybdate catalyst so long as it is commonly used in the art.

The metal precursor may be, for example, a metal salt including the corresponding metal, such as nitrate or ammonium salt of the corresponding metal.

In another example, bismuth (III) nitrate may be used as a bismuth precursor and ammonium molybdate may be used as a molybdenum precursor.

The bismuth nitrate is not well dissolved in water. Accordingly, bismuth nitrate can be dissolved by adding an acid to water. The acid is added in an amount to completely dissolve bismuth.

The acid is, for example, an inorganic acid, in another example, nitric acid.

The method of preparing the multi-component bismuth molybdate catalyst, for example, further comprises controlling a pH of the first mixed solution and/or the second mixed solution to a level enabling bismuth to be dissolved.

The reaction may comprise for example stirring under conditions of reaction temperature and reaction time that may be generally used for the production of the multi-component bismuth molybdate catalyst.

In another example, in the reaction step, the reaction temperature may be room temperature to 80° C., or 50 to 70° C. and the reaction time may be 5 minutes to 24 hours, or 10 minutes to 4 hours.

The drying may be for example carried out at 90 to 200° C. or 110 to 150° C. for 5 to 100 hours or 10 to 30 hours.

The calcining may be for example carried out within a temperature range of 400 to 600° C., 400 to 500° C., or 450 to 500° C.

In addition, the method of preparing 1,3-butadiene comprises a) charging the multi-component bismuth molybdate catalyst as a fixed bed in a reactor, and b) performing oxidative dehydrogenation while continuously passing a reactant comprising a butene-containing C4 mixture, air and steam over the catalyst layer of the reactor to prepare 1,3-butadiene.

The oxidative dehydrogenation is carried out at a reaction temperature of 250 to 350° C. and at a space velocity of 50 to 5,000 $h^{-1}$.

The multi-component bismuth molybdate catalyst obtained by adding Cs and K to the Mo—Bi—Fe—Co-based oxidation catalyst for production of butadiene from a butene mixture provides a butene conversion ratio of 95% or more and butadiene selectivity of 90% or more.

Hereinafter, preferred examples will be provided for better understanding of the present invention. The following examples are only provided to illustrate the present invention and it will be apparent to those skilled in the art that various modifications and alternations are possible within the scope and technical range of the present invention. Such modifications and alternations fall within the scope of claims included herein.

EXAMPLE

Examples 1 to 4

The metal precursors were used in amounts such that a molar ratio of Mo:Bi:Fe:Co:Cs:K was 10:1:1:8:0.5:0.015~0.12. Testing was performed by controlling the content of K while ratios of Mo, Bi, Fe, Co and Cs were fixed and the content of K with respect to each composition is shown in Table 1 below.

Bismuth nitrate pentahydrate ($Bi(NO_3)_3$ 5 ($H_2O$)), iron nitrate nonahydrate ($Fe(NO_3)_3.9(H_2O)$), cobalt nitrate hexahydrate ($Co(NO_3)_2.6\ (H_2O)$), potassium nitrate ($KNO_3$) and cesium nitrate ($CsNO_3$) were dissolved in distilled water to prepare a first solution. Separately, the bismuth nitrate pentahydrate was dissolved in an aqueous nitric acid solution and was then added.

In addition, ammonium molybdate tetrahydrate (($NH_4$)$_6$ ($Mo_7O_{24}$).4 ($H_2O$)) was dissolved in distilled water to prepare a second solution.

The first solution was added to the second solution, the resulting mixture was stirred at 40° C. for one hour to obtain a precipitate, and the precipitate was dried in an oven at 120° C. for 24 hours and then was calcined at 450° C. for 5 hours to prepare a multi-component bismuth molybdate catalyst.

A molar ratio of the components of the multi-component bismuth molybdate catalyst is Mo:Bi:Fe:Co:Cs:K=10:1:1:8:0.5:0.015~0.12, as shown in the following Table 1.

TEST EXAMPLE

The conversion ratio, butadiene selectivity and butadiene yield of bismuth molybdate catalysts prepared in Examples 1 to 9 described above and Comparative Examples 1 to 6 described below were measured in accordance with the following method and results are shown in Tables 1 to 4.

Trans-2-butene, cis-2-butene and oxygen were used as reactants, and nitrogen and steam were further fed. The reactor used herein was a metal tube reactor. The ratio of reactants and gas hourly space velocity (GHSV) were set based on 2-butene. A ratio of butene to oxygen to steam to nitrogen was set to 1:0.75:6:10 and GHSV was constantly controlled within the range of 50 to 75 $h^{-1}$ based on butene according to test conditions. A volume of the catalyst layer that the reactants contact was fixed at 200 cc, and the reactor was designed such that water was fed using a vaporizer and was evaporated into steam at 340° C., and the steam was mixed with 2-butene and oxygen as other reactants and was then fed to the reactor. The amount of butene was controlled using a mass flow controller for liquid, amounts of oxygen and nitrogen were controlled using a mass flow controller for gas, and the amount of steam was controlled while adjusting a feed velocity using a liquid pump. Reaction temperatures were maintained at 300° C., 320° C. and 340° C., and the product after reaction was analyzed by gas chromatography. The product contained, in addition to 1,3-butadiene as the target product, carbon dioxide, C4 by-products, and trans-2-butene, cis-2-butene and the like that remained unreacted. The conversion ratio of 2-butene, and selectivity and yield of 1,3-butadiene were calculated in accordance with the following Equations 1, 2 and 3.

$$\text{Conversion ratio (\%)} = \frac{\text{number of moles of reacted 2 - butene}}{\text{number of moles of supplied 2 - butene}} \times 100 \quad \text{EQUATION 1}$$

$$\text{Selectivity (\%)} = \frac{\text{number of moles of produced 1, 3 - butadiene}}{\text{number of moles of reacted 2 - butene}} \times 100 \quad \text{EQUATION 2}$$

$$\text{Yield (\%)} = \frac{\text{number of moles of produced 1, 3 - butadiene}}{\text{number of moles of supplied 2 - butene}} \times 100 \quad \text{EQUATION 3}$$

TABLE 1

| | Composition $Mo_{10}Bi_1Fe_1Co_8Cs_{0.5}+$ | SBR/OBR/NBR* | Temperature (° C.) | Pressure (psig) | Conversion ratio (%) | Selectivity (%) | Yield (%) | Hot spot (° C.) |
|---|---|---|---|---|---|---|---|---|
| Example 1 | $K_{0.015}$ | 1/4/12 | 320 | 12 | 99.5 | 90.53 | 90.08 | 392.5 |
| Example 2 | $K_{0.03}$ | 1/4/12 | 320 | 12 | 99.39 | 90.76 | 90.21 | 386.1 |
| Example 3 | $K_{0.06}$ | 1/4/12 | 320 | 12 | 98.05 | 91.79 | 89.99 | 376.9 |
| Example 4 | $K_{0.12}$ | 1/4/12 | 320 | 12 | 92.7 | 92.71 | 85.94 | 368.9 |

(*SBR: Steam/Butene, OBR = Oxygen/Butene, NBR = Nitrogen/Butene vol/vol ratio)

As can be seen from Table 1, when a predetermined amount of Cs was contained, conversion ratio and selectivity could be controlled by adding a relatively small amount of K (1/10 scale as compared to a case in which Cs was not contained) and conversion ratio was high and operation was easy at a low hot spot temperature when K was added together with Cs.

Comparative Examples 1 to 3: Addition of Only K to Composition of MoBiFeCo

The process was performed in the same manner as in Examples 1 to 4, except that Cs was not added and K was added in an amount shown in the following Table 2.

TABLE 2

| | Composition $Mo_{10}Bi_1Fe_1Co_8+$ | SBR/OBR/NBR | Temperature (° C.) | Pressure (psig) | Conversion ratio (%) | Selectivity (%) | Yield (%) | Hot spot (° C.) |
|---|---|---|---|---|---|---|---|---|
| Comparative Example 1 | $K_{0.1}$ | 0.75/6/14 | 320 | 12 | 91.30 | 88.66 | 80.94 | 405.1 |
| Comparative Example 2 | $K_{0.2}$ | 0.75/6/14 | 320 | 12 | 90.66 | 89.70 | 81.33 | 389.4 |
| Comparative Example 3 | $K_{0.4}$ | 0.75/6/14 | 320 | 12 | 93.78 | 90.73 | 90.73 | 397.9 |

As can be seen from Table 2 above, a relatively great amount of K should be added to control conversion ratio and selectivity, and normal operation was impossible due to excessively high hot spot temperature as compared to the conversion ratio when only K was added.

Examples 5 to 9: Addition of Both Cs and K to Composition of MoBiFeCo

The process was performed in the same manner as in Examples 1 to 4, except that a predetermined amount of K was added at a molar ratio of 0.06 and Cs was added in an amount shown in the following Table 3.

TABLE 3

| | Composition $Mo_{10}Bi_1Fe_1Co_8K_{0.06}+$ | SBR/OBR/NBR | Temperature (° C.) | Pressure (psig) | Conversion ratio (%) | Selectivity (%) | Yield (%) |
|---|---|---|---|---|---|---|---|
| Example 5 | $Cs_{0.12}$ | 1/4/12 | 320 | 8 | 99.75 | 90.34 | 90.12 |
| Example 6 | $Cs_{0.3}$ | 1/4/12 | 320 | 8 | 99.33 | 92.2 | 91.58 |
| Example 7 | $Cs_{0.45}$ | 1/4/12 | 320 | 8 | 99.26 | 92.21 | 91.53 |
| Example 8 | $Cs_{0.6}$ | 1/4/12 | 320 | 8 | 97.62 | 93.98 | 91.74 |
| Example 9 | $Cs_{0.7}$ | 1/4/12 | 320 | 8 | 95.42 | 93.4 | 89.12 |

As can be seen from Table 4 above, although K was added in a small amount (1/200 equivalent with respect to Mo), upon addition of Cs, conversion ratio and selectivity could be controlled to high levels (conversion ratio of 95% or more and selectivity of 90% or more). In the presence of K, selectivity was increased without great loss of conversion ratio caused by addition of Cs, and improvement of yield was thus possible by changing the composition.

Comparative Examples 4 to 5: Addition of Only Cs to Composition of MoBiFeCo

The process was performed in the same manner as in Examples 1 to 4, except that K was not added and Cs was added in an amount shown in the following Table 4.

TABLE 4

| | Composition $Mo_{10}Bi_1Fe_1Co_8+$ | SBR/OBR/NBR | Temperature (° C.) | Pressure (psig) | Conversion ratio (%) | Selectivity (%) | Yield (%) |
|---|---|---|---|---|---|---|---|
| Comparative Example 4 | $Cs_{0.25}$ | 1/6/14 | 320 | 12 | 99.57 | 85.93 | 85.56 |
| Comparative Example 5 | $Cs_{0.50}$ | 1/6/14 | 320 | 12 | 91.55 | 88.78 | 81.28 |

As can be seen from Table 4 above, selectivity was greatly decreased so as to obtain high conversion ratio when Cs was added in order to control conversion ratio and selectivity. In order to obtain high conversion ratio when only Cs was added, selectivity loss was great. This means that improvement of yield was not easy by control of Cs content.

Consequently, as can be seen from Tables 1 to 4 above, Examples 1 to 9 wherein the multi-component bismuth molybdate catalyst for production of butadiene comprises both K and Cs exhibited improved conversion ratio, selectivity and yield of butadiene and provided stability of process operation, even at a low hot spot temperature in spite of being used in a relatively small amount, as compared to Comparative Examples 1 to 6 in which the multi-component bismuth molybdate catalyst comprises only either Cs or K.

What is claimed is:

1. A multi-component bismuth molybdate catalyst for production of butadiene, comprising:
   bismuth;
   molybdenum;
   iron;
   cobalt;
   cesium; and potassium,
   wherein:
   the catalyst has the general formula:

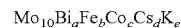
   $Mo_{10}Bi_aFe_bCo_cCs_dK_e$ wherein:
   a is 1, b is 1, c is 8, d is 0.3-0.7 and e is 0.06; or
   a is 1, b is 1, c is 8, d is 0.5 and e is 0.015-0.06.

2. A method of preparing 1,3-butadiene comprising:
   a) charging the multi-component bismuth molybdate catalyst for production of butadiene according to claim 1 as a fixed bed in a reactor; and b) performing oxidative dehydrogenation while continuously passing a reactant comprising a butene-containing C4 mixture, air and steam over the catalyst layer of the reactor to prepare 1,3-butadiene.

3. The method according to claim 2, wherein the oxidative dehydrogenation is carried out at a reaction temperature of 250 to 350° C. and at a space velocity of 50 to 5,000 $h^{-1}$.

* * * * *